(12) United States Patent
Tao et al.

(10) Patent No.: US 9,347,932 B2
(45) Date of Patent: May 24, 2016

(54) DEVICE AND METHOD FOR BREATH ANALYSIS USING ACOUSTIC RESONANCE FLOW RATE

(75) Inventors: Nongjian Tao, Fountain Hills, AZ (US); Francis Tsow, Tempe, AZ (US); Anant Rai, New Delhi (IN)

(73) Assignee: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 284 days.

(21) Appl. No.: 13/877,486

(22) PCT Filed: Oct. 3, 2011

(86) PCT No.: PCT/US2011/054574
§ 371 (c)(1),
(2), (4) Date: May 30, 2013

(87) PCT Pub. No.: WO2012/047792
PCT Pub. Date: Apr. 12, 2012

(65) Prior Publication Data
US 2013/0239655 A1 Sep. 19, 2013

Related U.S. Application Data

(60) Provisional application No. 61/389,388, filed on Oct. 4, 2010.

(51) Int. Cl.
*G01N 33/497* (2006.01)
*A61B 5/087* (2006.01)
*A61B 5/083* (2006.01)

(52) U.S. Cl.
CPC .............. *G01N 33/497* (2013.01); *A61B 5/087* (2013.01); *A61B 5/083* (2013.01)

(58) Field of Classification Search
CPC ......................... G01N 33/0037; G01N 33/497
USPC ........................................................ 73/23.3
See application file for complete search history.

(56) References Cited

U.S. PATENT DOCUMENTS

| 4,164,865 A | 8/1979 | Hall et al. |
| 4,603,589 A | 8/1986 | Machida |
| 5,599,713 A | 2/1997 | Sato |

(Continued)

FOREIGN PATENT DOCUMENTS

| EP | 1357879 | 12/2008 |
| EP | 2154526 | 2/2010 |

(Continued)

OTHER PUBLICATIONS

English Machine Translation of Yoshijirou et al., JP 08-014958 A, Jan. 1996, Translated May 2015.*

(Continued)

*Primary Examiner* — Hezron E Williams
*Assistant Examiner* — David Z Huang
(74) *Attorney, Agent, or Firm* — Fish & Richardson P.C.

(57) ABSTRACT

The present invention describes a device and method for measuring flow rate from air flow using acoustic resonance. It is shown that the device can be used to measure breath flow rate and biomarker concentration within human breath.

20 Claims, 6 Drawing Sheets

(56) References Cited

U.S. PATENT DOCUMENTS

| | | | |
|---|---|---|---|
| 5,853,005 | A | 12/1998 | Scanlon |
| 6,241,683 | B1 | 6/2001 | Macklem et al. |
| 6,272,905 | B1 | 8/2001 | Drzewiecki |
| 6,286,360 | B1 | 9/2001 | Drzewiecki |
| 6,863,068 | B2 | 3/2005 | Jamison et al. |
| 7,093,501 | B2 | 8/2006 | Kuo |
| 7,096,719 | B2 | 8/2006 | Gysling |
| 7,478,565 | B2 | 1/2009 | Young |
| 2002/0062681 | A1 | 5/2002 | Livingston |
| 2005/0101872 | A1 | 5/2005 | Sattler et al. |
| 2005/0183725 | A1 | 8/2005 | Gumaste et al. |
| 2006/0224421 | A1 | 10/2006 | St. Ores et al. |
| 2007/0086920 | A1* | 4/2007 | Anvar et al. ............ 422/87 |
| 2007/0208267 | A1 | 9/2007 | Schmid et al. |
| 2008/0167568 | A1 | 7/2008 | Rohde et al. |
| 2008/0208056 | A1 | 8/2008 | Kuhn et al. |
| 2009/0072835 | A1* | 3/2009 | Dorwarth ............ A47L 15/4297 324/448 |
| 2009/0281443 | A1 | 11/2009 | Hengstenberg et al. |
| 2009/0303058 | A1 | 12/2009 | Goodman et al. |
| 2011/0209551 | A1* | 9/2011 | Helldorfer .......... B60R 21/0132 73/658 |
| 2012/0143436 | A1* | 6/2012 | Cornet .................. G07C 5/085 701/33.4 |

FOREIGN PATENT DOCUMENTS

| | | |
|---|---|---|
| JP | 08014958 | 1/1996 |
| WO | WO 2004031761 | 4/2004 |
| WO | WO 2007065476 | 6/2007 |

OTHER PUBLICATIONS

Francesco, F. Di, et al., "Breath analysis: trends in techniques and clinical applications," Microchemical J., 2005, pp. 405-410, vol. 79.

Amorim, L. C. A., et al., "Breath air analysis and its use as a biomarker in biological monitoring of occupational and environmental exposure to chemical agents," J. Chromatogr. B, 2007, pp. 1-9, vol. 853.

Chan, Hiang Ping, et al., "Exhaled breath analysis: Novel approach for early detection of lung cancer," Lung Cancer, 2009, pp. 164-168, vol. 63.

Mashir, Alquam, et al., "Exhaled breath analysis: The new interface between medicine and engineering," Advanced Powder Technology, 2009, pp. 420-425, vol. 20.

International Search Report and Written Opinion for PCT Application No. PCT/US2011/054574, 12 pages.

International Preliminary Report on Patentability for PCT Application No. PCT/US2011/054574, 7 pages.

* cited by examiner

DEVICE AND METHOD FOR BREATH ANALYSIS USING ACOUSTIC RESONANCE FLOW RATE

CROSS-REFERENCE TO RELATED APPLICATIONS

This application is a U.S. National Phase Application of International Patent Application No. PCT/US2011/054574 filed Oct. 3, 2011, which claims the benefit of U.S. Provisional Application No. 61/389,388, filed on Oct. 4, 2010, the contents of both of which are incorporated herein by reference in their entirety.

TECHNICAL FIELD

The present invention relates to devices and methods of use for monitoring of exhaled breath, detection of biomarkers from breath, and diagnostic health monitoring.

BACKGROUND

The control and monitoring of gas flow is important in many applications, from fluid transport and delivery, to medical applications such as breath analysis, for anesthesiology and diagnostic monitoring.

Volatile organic compounds (VOCs) are a diverse group of carbon-based chemicals that are volatile at ambient temperature. VOC analysis is used in the fields of environmental contamination monitoring, forensic science, mining, chemical manufacture and process control, and fragrance and flavor industries. VOCs emitted from breath may include biomarkers useful in the diagnosis of a plurality of diseases, including but not limited to asthma, breast cancer, chronic obstructive pulmonary disease, diabetes, schizophrenia, cystic fibrosis, and arthritis. For example Nitric Oxide (NO), Pentane, ethane, and 8-isoprotane have been found as potential diagnostic markers in human breath of patients with asthma, while acetone, ethanol, and methyl nitrate have been found in diabetes. Other VOCs that could be used as biomarkers in breath include, but are not limited to carbon dioxide, oxygen, and ammonia.

In general, biomarker monitoring offers a lower cost, less invasive method of obtaining important medical information from a patient. Since the discovery of NO in human breath, it has been quite intensively studied with association in allergen-induced airway inflammation, as a marker of eosinophilic airway inflammation, and its utility to assess response to anti-inflammatory therapy. NO levels are affected by age, height, weight, gender, and race and NO is generally free of day-to-day variation making it highly reproducible. Also, NO concentrations in exhaled breath are dependent on the flow rate making NO the most widely studied and standardized noninvasive biomarker for asthma.

Biomarker analysis through exhaled-breath monitoring has not yet been introduced into every day diagnostic clinical practice. This is mainly due to the lack of standardization and normalization of sampling procedures and the lack of a uniformly accepted evaluation criteria for data. However, with the recent development of flow rate sensors, measurement of biomarkers such as NO has been greatly simplified.

The alternative to assessing airway inflammation is bronchial biopsy which is expensive, invasive, complex, and not widely available to physicians. Bronchial biopsy does not fit the trend of moving towards non-invasive and rapid diagnostic tools which are simpler to perform, painless, and more agreeable to patients. This new trend opens up a new promising area for a noninvasive diagnostic tool with various advantages. Tests can be repeatedly performed without discomfort to patients. They also can be applied to children including infants and to patients with severe disease in whom more invasive procedures are not possible.

Existing methods and devices may detect such unknown biomarkers, but they are generally slow and complicated. Miniaturized sensors and methods generally lack sufficient sensitivity, selectivity, and/or reliability; and may be especially deficient for detecting one or more biomarkers in human breath.

Even though flow sensors can be quite affordable, a simpler, less expensive and more reliable sensor can be tremendously useful, particularly in applications targeting in-home medical treatment/management tools. Other flow sensors in the art tend to use complicated detection methods such as thermal mass transport based, optical based, mechanical (both flow and pressure based), Doppler, electromagnetic, and Coriolis effects. One of the more common techniques to measure flow rate is using an ultrasound transducer.

U.S. Pat. No. 4,603,589 uses two ultrasound bi-directional transducers, each include transmitting and receiving circuits, to measure the flow parameters between the two transducers. The international patent application WO 2007/065476 also uses two ultrasound bi-directional transducers but instead calculates a mass flow of gas by obtaining time of flight signals for the upstream and downstream. U.S. Pat. No. 2002/0062681 uses two ultrasound transducers, one near the gas inlet port to a gas flow path and one near the outlet of the gas outlet port. A microcontroller compares the difference in time between the ultrasonic pulse from the ultrasound transducer near the inlet and the ultrasound transducer near the outlet and measures the concentration of gas flowing through the device.

The above prior art systems incorporate ultrasound or time and flight or a combination of both to calculate gas concentration or flow rates. These methods involve complicated and expensive circuitry and electronics.

Thus, there is a need in the art for a simple and inexpensive technology for measuring air flow, one that can be reliably integrated with a sensor system for biomarker monitoring.

BRIEF SUMMARY OF THE INVENTION

The present invention addresses a need for a novel, simple, reliable, low cost, acoustic resonance flow rate measurement method and device.

The present invention is an improvement over other those flow sensors and others in its simplicity, mobility and versatility. The invention uses very simple and low cost electronics that do not require flow information to travel upstream and downstream, but rather in a linear direction, for quick, easy results. In terms of versatility, the invention can be a standalone device or built into part of system that needs to be monitored with minimal additional costs. The present invention can also be attached to a cellular phone; opening the door to a variety of applications. The invention could make a significant impact in developing countries as a stand-alone device or by taking advantage of the spread of cell phones worldwide.

In a first aspect, the present invention relates to a device for measuring flow rate from air flow using acoustic resonance. The device can be used to measure breath flow rate, and can be further integrated with other sensor platforms to measure any gaseous biomarkers from human breath. Those biomarkers can be, for example, NO, oxygen, carbon dioxide, acetone, and ammonia.

Thus the invention provides a device for measuring flow rate in air flow comprising: a flow sensor containing an audio transducer, an acoustic chamber; an acoustic sensor connected to the flow sensor; and a processor connected to the acoustic sensor, wherein the device is comprised of a housing that allows for the conversion of flow information into an characteristic acoustic signal, wherein the acoustic sensor picks up the characteristic acoustic signal, and wherein the acoustic sensor is linked to a processor that analyzes said acoustic signal using acoustic resonance.

The flow sensor contains a housing with an inlet for receiving a sample gas, an outlet and an acoustic chamber in between the gas inlet and the gas outlet. The audio transducer is located near the inlet of the acoustic chamber and capable of transmitting an acoustic signal through the acoustic chamber towards the gas outlet. The gas outlet is a narrow opening, creating backpressure within the acoustic chamber thus slowing flow rate and causing a linear relationship between flow rate and frequency.

The housing is made of a material such a polymer material, but can be constructed of any material known in the art for use in construction of medical devices, such as metal, ceramic, wood, composites, or mixtures thereof.

The audio transducer is created by standard fabrication techniques [1] such as building an acoustic flute or other standard flute fabrication techniques. Materials such as plastics are used to fix the audio transducer to the acoustic chamber.

The audio transducer can be an acoustic flute, a whistle, or a single reed instrument.

The acoustic sensor can be any standard microphone, an A/D converter, or the human ear.

The processer can be a computer, a cell phone, or a human brain.

In another aspect, the present invention also provides a method for measuring breath flow rate and biomarker concentrations using acoustic resonance comprising receiving air flow into the flow sensor of the device, thereby creating a backpressure; converting the flow information into an acoustic signal to be picked up by the acoustic sensor of the device; and sending the acoustic signal to the processor of the device to determine the presence of the biomarker in the breath.

This device could be used as a means for breath biomarker analysis; providing critical information to asthma patients as a way to measure NO concentrations in breath. Patients can monitor their NO concentrations with a simple device without leaving the comfort of their home. Such a device could be a stand alone device or conveniently built into existing devices and be molded into part of the housing, thus having potentially high impact applications in both developed and underdeveloped countries.

In specific embodiments, the biomarker is Nitric Oxide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

EXPERIMENTAL PROCEDURES

Air, either from a gas cylinder or human breath, was introduced at unknown flow rate through our acoustic sensor in series with a calibrated commercial flow sensor. Acoustic output from our flow sensor was recorded with a microphone which was connected to a computer. Digital output from the commercial flow sensor was recorded simultaneously with the same computer to compare with results from our flow sensor.

BRIEF DESCRIPTIONS OF THE FIGURES

DETAILED DESCRIPTION OF EXEMPLARY EMBODIMENTS

In a first aspect, the present invention provides a device for measuring flow rate from a gas source using acoustic resonance. The device contains a flow sensor into which the gas is collected. The flow sensor has a housing comprising a gas inlet for receiving a gas sample, an outlet configured to produce a backpressure dependant on gas flow, and an acoustic chamber between the gas inlet and the gas outlet. The audio transducer, created by standard fabrication techniques, is located near the inlet of an acoustic chamber. An acoustic sensor can be located anywhere where the generated acoustic signal can be picked up. There is also a processor connected to the acoustic sensor. The device also has the potential to measure biomarkers within human breath when apparatus described is arranged to measure exhaled breath from patients.

Figure 1:
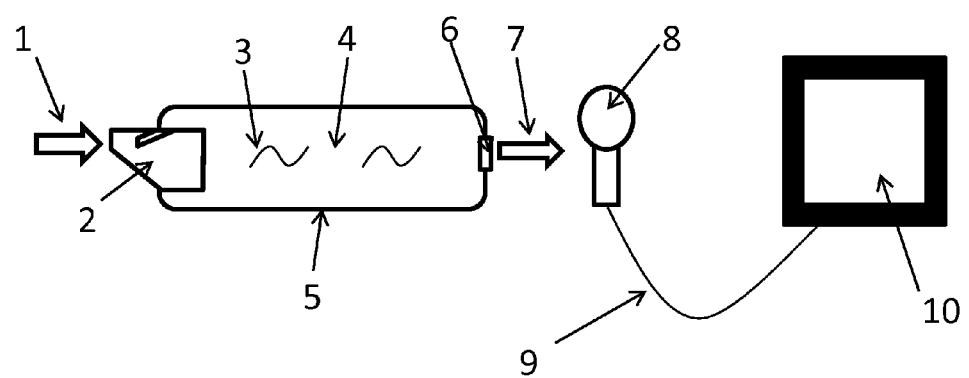
FIG. 1 shows a schematic arrangement for measuring flow rate according to the present invention.

Referring to the drawings in particular, FIG. 1 shows a schematic arrangement for measuring flow rate according to the present invention. A flow sensor housing 5 is arranged between a gas source 1 and an outlet 6. A gas source 1 enters through the audio transducer 2, which acts as a gas flow inlet generating a characteristic acoustic signal 3 depending on the flow rate of the gas. The audio transducer 2 and the gas flow outlet 6 are configured to produce a back-pressure within the acoustic chamber 4 dependant on the gas flow. The acoustic signal 3, which is modulated by the back-pressure, travels through the acoustic resonance chamber 4 exiting through the gas outlet 6 creating an acoustic output 7 that can be picked up by a microphone 8 located near the gas outlet 6. The microphone 8 is connected to a computer 10 by a wired connection 9. The computer 10 analyzes the flow rate of the gas source based on the frequency of the acoustic sound.

Figure 2:
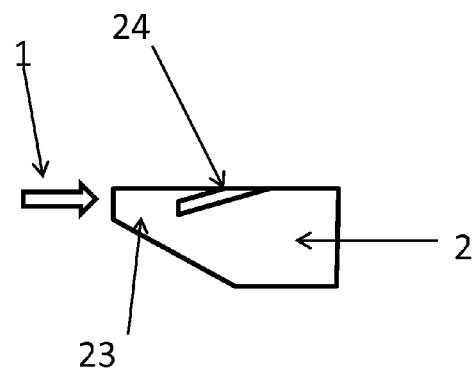
FIG. 2 shows a schematic view of a vibrating reed acting as audio transducer as a means for creating an acoustic sound.
Figure 3:
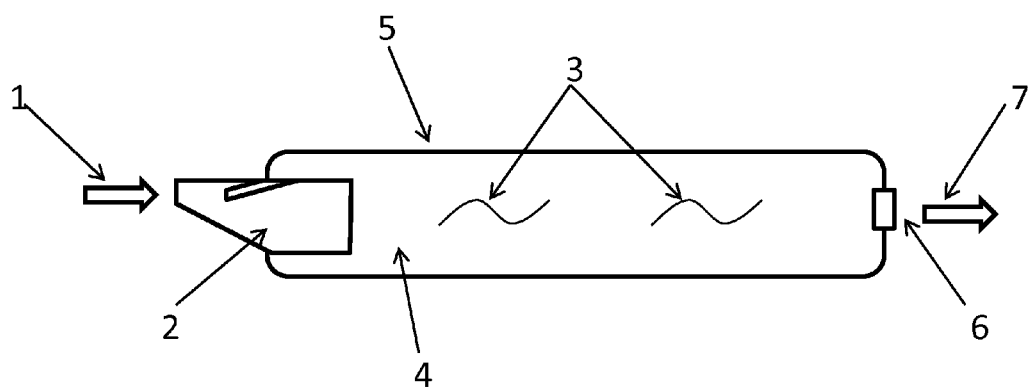
FIG. 3 shows a schematic view of a vibrating reed acting as an audio transducer within the flow sensor.

FIG. 2 shows a schematic view of a vibrating reed acting as an audio transducer as a means for creating an acoustic sound. The gas source 1 enters the mouthpiece 23, which contains a reed 24 on the upper wall of the audio transducer 2. The reed 24 oscillates generating an acoustic signal whose frequency and intensity depends on the direction and the speed of the gas flow. Now, referring to FIG. 3 which shows a schematic view of a vibrating reed acting as an audio transducer within the flow sensor. The audio transducer 2 including the vibrating reed 24 is attached to the inlet of the flow sensor housing 5 allowing the acoustic signal 3, which is modulated by the back-pressure, to travel through the acoustic resonance chamber 4 exiting through the gas outlet 6 creating an acoustic output 7. The acoustic output 7 can be picked up by the human ear and analyzed by the human brain.

Figure 4:
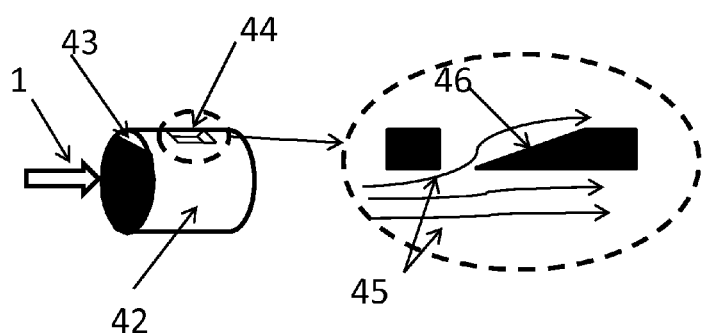
FIG. 4 shows a schematic view of a whistle acting as an audio transducer as a means for creating an acoustic sound.
Figure 5:
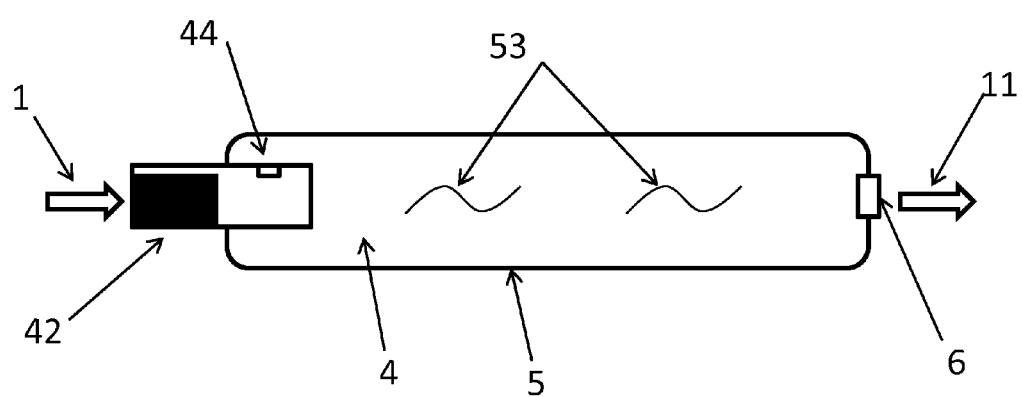
FIG. 5 shows a schematic view of a whistle acting as an audio transducer within the flow sensor.

FIG. 4 shows a schematic view of a whistle 42 acting as an audio transducer as a means for creating an acoustic sound. The gas source 1 enters the narrow air channel 43 and travels towards the outlet 44, which contains a notch 46. The air flow 45 moves above and below the notch 46 causing the notch 46 to oscillate, thus generating an acoustic sound. The acoustic sound's frequency and intensity depend on the direction and speed of the gas flow. Now, referring to FIG. 5 which shows a schematic view of the whistle 42 acting as an audio transducer within the flow sensor. The whistle 42 is attached to the inlet of the flow sensor housing 5 allowing the acoustic signal 53, which is modulated by the back-pressure, to travel through the acoustic resonance chamber 4 exiting through the gas outlet 6 creating an acoustic output 11. The acoustic output 11 can be picked up by the human ear and analyzed by the human brain. The device can also be used with a microphone and a processor as shown by FIG. 1.

Figure 6:
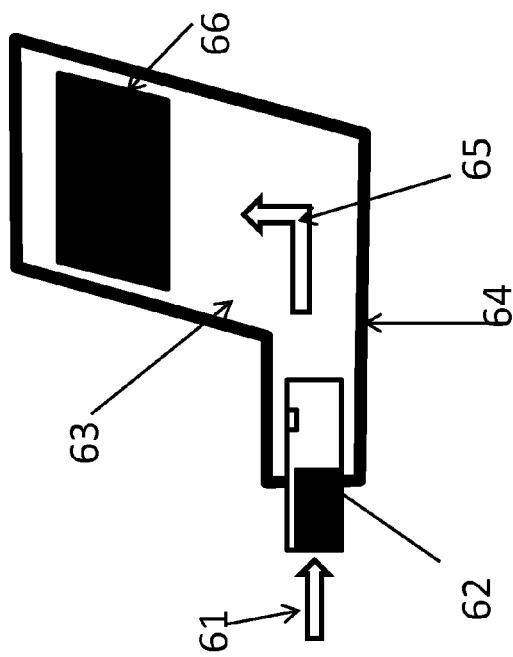
FIG. 6 shows a schematic view of a breath sensor for measuring breath flow rate and biomarkers in human breath.

FIG. 6 shows a schematic view of a breath sensor for measuring breath flow rate and biomarkers in human breath. Exhaled breath 61 enters through the audio transducer 62, which acts as a gas flow inlet generating a characteristic acoustic signal 65 depending on the flow rate of the exhaled gas. The acoustic signal 65, which is modulated by the back-pressure, travels through the acoustic resonance chamber 63. Chemical information is measured through chemical analysis, and is analyzed by the chemical sensor 66, which is within the flow sensor housing 64 and the biomarker concentration of the specified analyte can be determined by the flow rate of the breath.

In operation, the exhaled breath, containing the biomarker or analyte of interest is exposed to the device. The term "analyte" refers to a substance being tested. Examples of measurable analytes to be measured by the device of the invention include NO, oxygen, carbon dioxide, acetone, and ammonia.

The device for measuring flow rate from a gas source using acoustic resonance can be optimized such that an audible sound to humans, between the frequencies of 12 Hz and 20,000 Hz, will only be produced within a given range of flow rates. This would be particularly useful in applications where measurements have to be made within a specified range of flow rate for the measurement to be valid, such as NO measurements in asthmatic patients. For sounds waves that cannot be picked up by the human ear, the audible sound can be picked up by a suitable acoustic sensor, sensitive to the specific acoustic frequency range. The sensor would blink if the specified range is met. Having the sensor give such feedback allows for a user-friendly feature by producing an audible sound or a blinking light, or both only when the device is used properly. This would be particularly useful in home medical treatment applications where patients may not have professional assistance and still require a reliable and accurate NO measurement.

Figure 7:
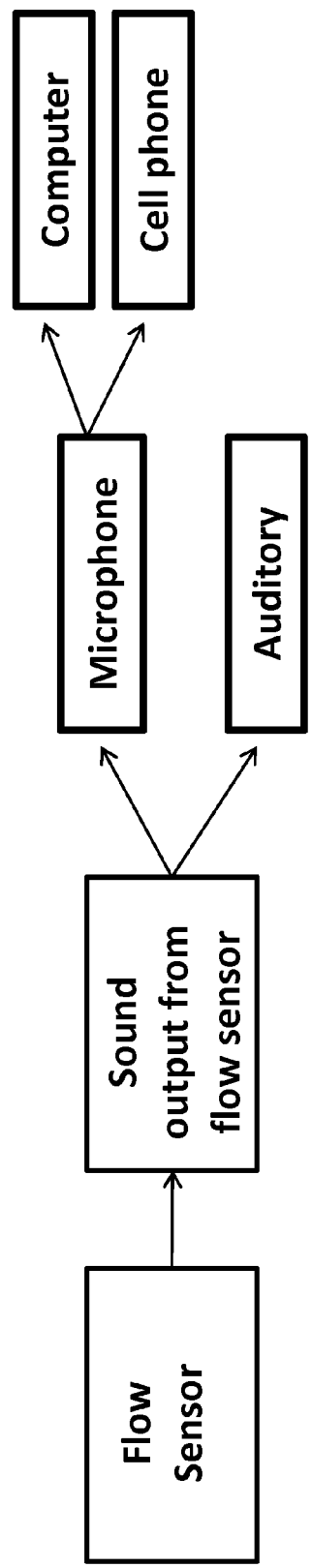
FIG. 7 shows a block diagram for picking up acoustic output from the flow sensor.
Figure 8:
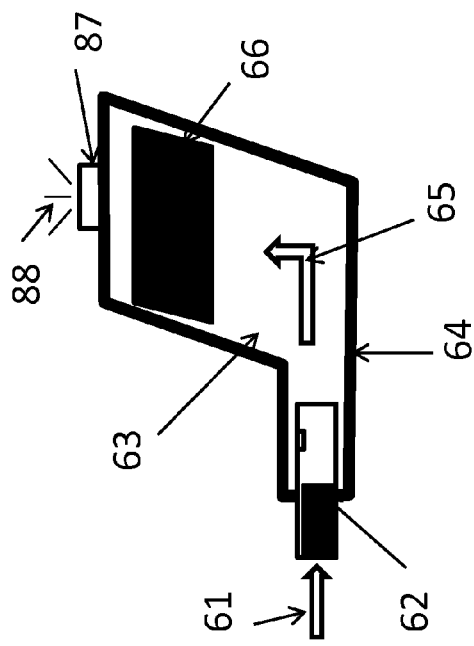
FIG. 8 shows a schematic view of a breath sensor for measuring breath flow rate and biomarkers in human breath with an acoustic sensor attached.

FIG. 7 shows a block diagram for picking up acoustic output from the flow sensor. An acoustic sound exits the flow sensor and is picked up auditory or by a microphone. If a microphone is used a computer or a cell phone is used to analyze the flow rate of the gas. If the acoustic sound is picked up auditory then the human brain analyzes the flow rate of the gas. In such an embodiment an acoustic sensor would be helpful in determining if a specific acoustic range is met. Referring to FIG. 8 which shows a schematic view of a breath sensor for measuring breath flow rate and biomarkers in human breath with an acoustic sensor attached. The exhaled breath 61 enters the acoustic resonance chamber 63 through the audio transducer 62. Chemical information is measured through chemical analysis, and is analyzed by the chemical sensor 66, which is within the flow sensor housing 64, only if a specific acoustic frequency range is met. The acoustic sensor 87 acts as such a threshold for chemical analysis. If the specific acoustic frequency is met then the acoustic sensor 87 will emit a visual cue in the form of a blinking light 88.

Figure 9:
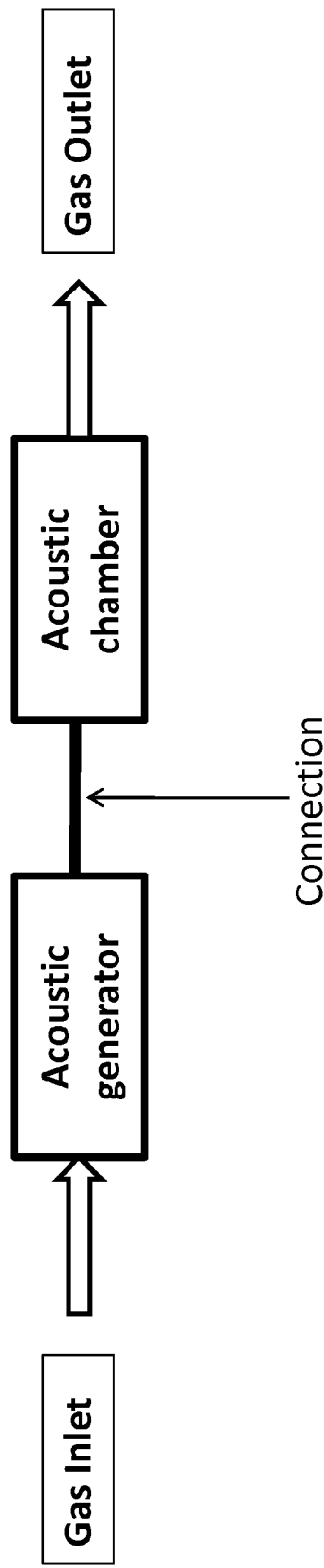
FIG. 9 shows a block diagram of the direction of the acoustic signal within the flow sensor.

FIG. 9 shows a block diagram of the direction of the acoustic signal within the flow sensor. The gas enters the acoustic generator creating a characteristic acoustic signal depending on the flow rate of the gas. The acoustic sound enters the acoustic chamber, which is connected to the acoustic generator and exits through the gas outlet.

Figure 10:
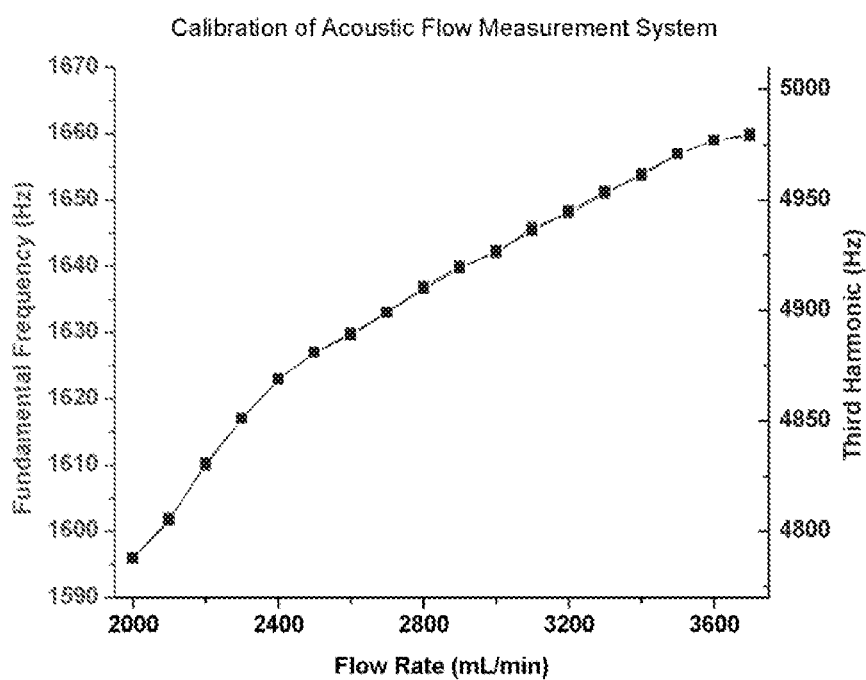
FIG. 10 shows the calibration of the device measuring flow rate (milliliter per minute) against the fundamental frequency (Hertz). The graph shows a linear relationship between flow rate and frequency.

FIG. 10 shows the calibration of the device measuring flow rate (milliliter per minute) against the fundamental frequency (Hertz). An air cylinder was used to create an air flow to measure against fundamental frequency. The graph shows a monotonically linear relation between flow rate and frequency.

In addition, the present invention could also be used in a variety of other fields. For example, in measuring wind speeds, temperatures, or humidity. Knowledge of wind speeds could be very useful in a variety of sports including but not limited to golf, sailing, surfing, and windsurfing.

The device offers a simple and cost efficient method for obtaining flow rate measurements from biomarkers in breath to wind speeds, temperatures, and humidity.

REFERENCES

1. "How to Make a Flute." *eHow*. n.d. 23 Jun. 2010. <http://www.ehow.com/how_4441928_make-flute.html>

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A device for measuring gas flow for chemical analysis, comprising:
   at least one acoustic generator;
   an acoustic chamber connected to said acoustic generator, wherein said acoustic chamber comprises at least one gas flow inlet and at least one gas flow outlet configured to produce a back-pressure dependent on gas flow;

a chemical sensor coupled to the acoustic chamber, the chemical sensor configured to measure an analyte in the gas flow in response to the gas flow having an acoustic frequency in a specific acoustic frequency range; and an acoustic sensor coupled to the acoustic chamber, the acoustic sensor configured to measure the acoustic frequency produced by the gas flow and to provide an indication of the gas flow being in the specific acoustic frequency range.

2. The device of claim 1, wherein said acoustic generator comprises an acoustic flute, a single reed instrument, or a whistle.

3. The device of claim 1, wherein the chemical sensor comprises a nitric oxide (NO) sensor.

4. The device of claim 1, wherein the acoustic sensor is configured to measure the acoustic frequency of gas having a gas flow rate in the range of 2000 milliliter per minute to 3000 milliliter per minute.

5. The device of claim 1, wherein the acoustic sensor comprises at least one of a microphone and an A/D converter.

6. The device of claim 5, wherein the acoustic sensor is operably linked to a processor for measurement of air flow rate using acoustic resonance.

7. The device of claim 6, wherein said processor comprises at least one of a computer and a cell phone.

8. The device of claim 1, arranged to measure exhaled-breath from a patient.

9. A method for measuring exhaled breath air flow comprising:

receiving exhaled breath flow into a flow sensor housing forming an acoustic chamber, the flow sensor housing including an acoustic generator connected to an inlet, the flow sensor housing, housing a chemical sensor;

generating a back-pressure in the acoustic chamber;

producing an acoustic signal in the acoustic chamber, wherein said acoustic signal is modulated by the back-pressure;

detecting said acoustic signal with an acoustic sensor;

analyzing said acoustic signal to determine if the exhaled breath flow is in a specific acoustic frequency range; and measuring an analyte in the exhaled breath flow via a chemical sensor, in response to a determination that the exhaled breath flow is in the specific acoustic frequency range.

10. The method of claim 9, where the chemical sensor comprises an NO sensor.

11. The method of claim 9, wherein analyzing the acoustic signal to determine if the exhaled breath flow is in a specific acoustic frequency range includes analyzing the acoustic signal via a cell phone.

12. The method of claim 9, wherein analyzing the acoustic signal to determine if the exhaled breath flow is in a specific acoustic frequency range includes analyzing the acoustic signal via a computer.

13. The method of claim 9, further comprising producing the acoustic signal via an acoustic generator.

14. The method of claim 13, wherein the acoustic generator includes a vibrating reed.

15. A device for measuring gas flow for chemical analysis, comprising:

at least one acoustic generator comprising a vibrating reed configured to oscillate to generate an acoustic signal based on a gas flow;

an acoustic chamber connected to the acoustic generator, the acoustic chamber comprising at least one gas flow inlet and at least one gas flow outlet configured to produce a back-pressure dependent on the gas flow; and a chemical sensor positioned in the acoustic chamber, the chemical sensor configured to measure an analyte in the gas flow in response to the gas flow having an acoustic frequency in a specific acoustic frequency range; and an acoustic sensor coupled to the acoustic chamber, the acoustic sensor configured to measure the acoustic frequency produced by the gas flow and to provide an indication of the gas flow being in the specific acoustic frequency range.

16. The device of claim 15, wherein the chemical sensor comprises a nitric oxide (NO) sensor.

17. The device of claim 15, wherein the acoustic sensor is configured to measure the acoustic frequency of gas having a gas flow rate in the range of 2000 milliliter per minute to 3000 milliliter per minute.

18. The device of claim 15, wherein the specific acoustic frequency range includes 12 Hertz to 20,000 Hertz.

19. The device of claim 15, wherein the chemical sensor is configured to measure a plurality of analytes.

20. The device of claim 15, wherein the chemical sensor is configured to measure one or more analytes selected from the group consisting of: nitric oxide, oxygen, carbon dioxide, acetone, and ammonia.

* * * * *